US008961759B2

(12) United States Patent
Burke et al.

(10) Patent No.: US 8,961,759 B2
(45) Date of Patent: Feb. 24, 2015

(54) DEVICE AND METHOD FOR MITOCHONDRIAL MEMBRANE POTENTIAL ASSESSMENT

(75) Inventors: Peter Burke, Irvine, CA (US); Tae-Sun Lim, Hillsboro, OR (US); Antonio Davila, Philadelphia, PA (US); Douglas C. Wallace, Swarthmore, PA (US); Katayoun Zand, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 317 days.

(21) Appl. No.: 13/412,515

(22) Filed: Mar. 5, 2012

(65) Prior Publication Data

US 2012/0247980 A1    Oct. 4, 2012

Related U.S. Application Data

(60) Provisional application No. 61/451,370, filed on Mar. 10, 2011.

(51) Int. Cl.
*G01N 27/414* (2006.01)
*G01N 27/403* (2006.01)
*G01N 33/483* (2006.01)

(52) U.S. Cl.
CPC ........ *G01N 27/4035* (2013.01); *G01N 33/4833* (2013.01); *Y10S 435/82* (2013.01)
USPC ......... 204/418; 204/416; 422/82.03; 435/820

(58) Field of Classification Search
CPC . Y10S 436/806; Y10S 435/82; G01N 27/333; G01N 27/414; G01N 27/4035; C12Q 2565/607; C12Q 2565/629; B01J 19/0093; B01L 2300/0645; B01L 2300/0636; B01L 3/5027
USPC ............ 204/416–420; 422/82.03; 435/317.1, 435/820; 436/806
See application file for complete search history.

(56) References Cited

PUBLICATIONS

T.-S. Lim, et al. "Assessment of mitochondrial membrane potential using an on-chip microelectrode in a microfluidic device", Lab on a Chip, vol. 10, No. 13, Jul. 2010, p. 1683-1688.*
A. Baracca, et al. "Rhodamine 123 as a probe of mitochondrial membrane potential: evaluation of proton flux through Fo during ATP synthesis", Biochimica Et Biophysica ACTA, vol. 1606, 2003, p. 137-146.*
R. C. Scaduto, Jr. and L. W. Grotyohann, "Measurement of mitochondrial membrane potential using fluorescent rhodamine derivatives", Biophysical Journal, vol. 76, Jan. 1999, p. 469-477.*

(Continued)

*Primary Examiner* — J. Christopher Ball
(74) *Attorney, Agent, or Firm* — Vista IP Law Group LLP

(57) ABSTRACT

A microfluidic sensor device includes a substrate having patterned thereon at least one Ag/AgCl electrode (working electrode) and an inner chamber overlying the at least one Ag/AgCl electrode. The device includes an ion selective permeable membrane permeable to TPP$^+$ disposed on one side of the first chamber and a sensing chamber overlying the ion selective permeable membrane. A separate reference electrode is inserted into the sensing chamber. The working electrode and reference electrode are coupled to a voltmeter to measure voltage. This voltage can then be translated into a TPP$^+$ concentration which is used to determine the mitochondrial membrane potential ($\Delta\Psi_m$).

29 Claims, 13 Drawing Sheets

(56) References Cited

PUBLICATIONS

A. Baez-Ruiz, et al. "Metabolic adaptations of liver mitochondria during restricted feeding schedules", AJP- Gastrointestinal Liver Physiology, vol. 289, 2005, p. G1015-1023.*

Duchen, M. R., Mitochondria in health and disease: perspectives on a new mitochondrial biology, Molecular Aspects of Medicine, 25, 365-451, (2004).

Kamo, N. et al. Membrane Potential of Mitochondrial Measured with an Electrode Sensitive to Tetraphenyl Phosphonium and Relationship between Proton Electrochemical Potential and Phosphorylation Potential in Steady State, J. Membr. Biol. 1979, 49, 105-121.

Labajova, A. et al., Evaluation of mitochondrial membrane potential using a computerized device with a tetraphenylphosphonium-selective electrode, Anal. Biochem., 2006, 353, 37-42.

Nicholls, D.G.,The influence of respiration and ATP hydrolysis on the proton electrochemical gradient across the inner membrane of rat liver mitochondria as determined by ion distribution, European Journal of Biochemistry 50, 305-315, (1974).

Perry, S. W. et al., Mitochondrial membrane potential probes and the proton gradient: a practical usage guide, Biotechniques,50(2),98-115, (2011).

Reers, M. et al., Mitochondrial membrane potential monitored by JC-1 Dye, Methods in Enzymology, 260, 406-417, (1995).

Scaduto, R. C. et al., Measurement of Mitochondrial Membrane Potential Using Fluorescent Rhodamine Derivatives, Biophysical Journal, 76, 469-477, (1999).

Trounce, I. A. et al., Assessment of mitochondrial oxidative phosphorylation in patient muscle biopsies, lymphoblasts, and transmitochondrial cell lines, Methods Enzymol, vol. 264, pp. 484-509, 1996.

Zillberstein, D. et al., Proton electrochemical gradient in *Escherichia coli* cells and its relation to active transport of lactose, 18(4), 669-673, (1979).

Satake, Hiromu et al., A Coated Wire Electrode Sensitive to Tetraphenylphosphonium Ion for Measurement of the Mitochondrial Membrane Potential, Analytical Letters, 24(2), 295-304 (1991).

* cited by examiner

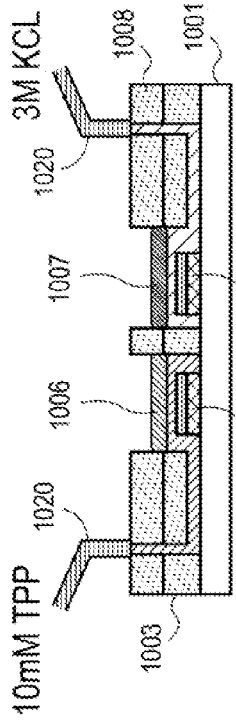
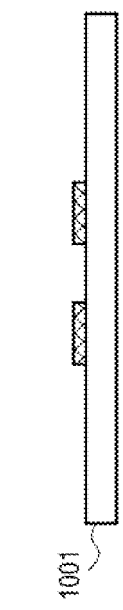
FIG. 13A
FIG. 13B
FIG. 13C
FIG. 13D
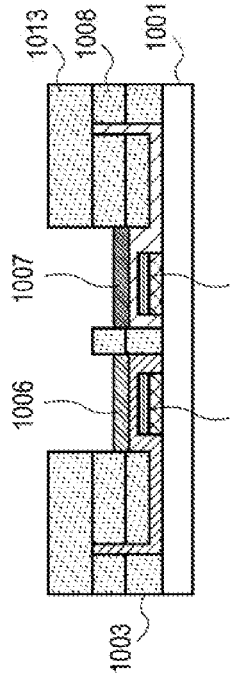
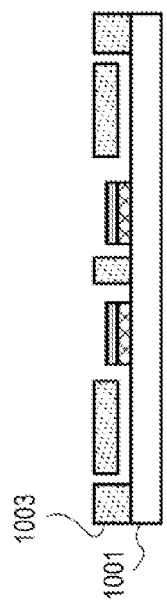
FIG. 13E
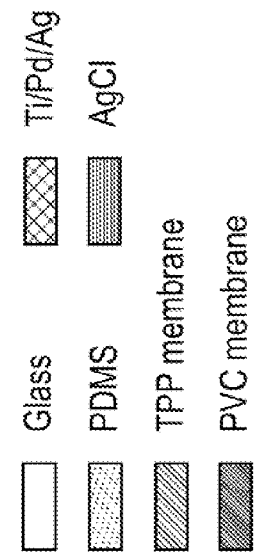
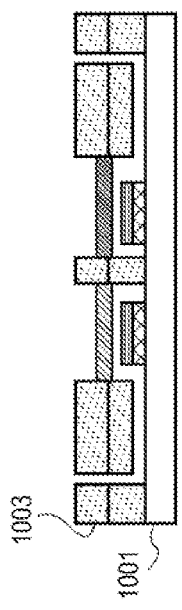
FIG. 13F

DEVICE AND METHOD FOR MITOCHONDRIAL MEMBRANE POTENTIAL ASSESSMENT

RELATED APPLICATION

This application claims priority to U.S. Provisional Patent Application No. 61/451,370, filed on Mar. 10, 2011, which is hereby incorporated by reference in its entirety Priority is claimed pursuant to 35 U.S.C. §119.

STATEMENT REGARDING FEDERALLY SPONSORED RESEARCH OR DEVELOPMENT

This invention was made with government support under grants AG024373, NS021328, AG013154. DK073691 and CA143351 awarded by the National Institute of Health, and grant W911NF-11-1-0024 awarded by the US Army Research Office. The government has certain rights in the invention.

FIELD OF THE INVENTION

The field of the invention generally relates to devices and methods for measurement of mitochondrial membrane potential, and more particularly to the fabrication and use of a lab-on-a-chip device to measure mitochondrial membrane potential.

BACKGROUND

The mitochondrial membrane potential ($\Delta\Psi_m$) plays a crucial role in the production of ATP as an energy source of the cell. The electron transport chain (complex I, II, III, IV) positioned at the mitochondrial inner membrane generates this electrochemical potential gradient across the inner membrane by pumping protons through the mitochondrial inner membrane while sequentially transporting electrons through the complexes. This proton gradient is utilized by ATP synthase (complex V) to synthesize ATP from ADP and inorganic phosphate. This cycle can remain functional and constantly produces ATP to sustain the cell only when the electrochemical proton gradient is maintained at a constant level with enough available ADP. $\Delta\Psi_m$ is the key component of this electrochemical potential gradient.

Mitochondria are known to regulate cell life and death through control of apoptosis, through a critical, irreversible step involving the mitochondrial permeability transition pore (mPTP), a megapore complex triggered to open under certain conditions at both the mitochondrial inner and outer membrane. Once opened, the permeability of the mitochondrial inner membrane increases drastically, causing the release of bioactive proteins including cytochrome C and the inflow of protons, resulting in an irreversible collapse of the mitochondrial membrane potential. This process is known to lead to apoptosis or cell death. In addition, malfunctions and abnormal behaviors of mitochondria are highly associated with the degenerative diseases and the aging process.

To date, various methods have been used to measure $\Delta\Psi_m$ based on either fluorescent probes or electrochemical methods. For example, rhodamine dyes (e.g., Rhodamine-123), carbocyanins, merocyanines, and oxonols have been used as fluorescent molecular probes to measure $\Delta\Psi_m$. Nano-electrodes used to impale the mitochondrial membrane in a patch clamp type assay are challenging. Many measurements to date have been based on assays of the distribution of lipophilic probe ions across the membrane, whose concentration ratio is related to $\Delta\Psi_m$ through the Nernst equation. The probe ion concentration ratio is either measured through changes in fluorescence intensity (using cytofluorometry, confocal microscopy, fluoroescence microscopy, or fluoroescence spectroscopy) or electrochemically through ion selective electrodes (ISE).

Kamo et al. first reported an ISE membrane potential electrode using tetraphenylphosphonium (TPP$^+$) ions, a lipid-soluble cation, and found that TPP$^+$ can permeate through mitochondrial membranes with 15 times faster diffusion coefficient than other cations such as DDA$^+$ (debenzyldimethyl ammonium). See N. Kamo, M. Muratsugu, R. Hongoh and Y. Kobatake, *J. Membr. Biol.*, 1979, 49, 105-121. Since the accumulation of TPP$^+$ ions into the mitochondrial matrix is related to $\Delta\Psi_m$ through the Nernst equation and volumetric factors, its value can be determined from the concentration of TPP$^+$ ions.

TPP$^+$ ions diffuse through the mitochondrial inner membrane, the concentration ratio depending on $\Delta\Psi_m$, determined by the Nernst equation, i.e.

$$\frac{[TPP]_{out}}{[TPP]_{in}} = e^{\frac{\Delta\Psi_m}{kT}} \qquad (1)$$

By measuring the concentration of TPP outside the mitochondria (referred to as "[TTP]$_{out}$") using electrochemical ion selective electrode technology one can infer the amount of cation taken up into the mitochondria, (hence termed "[TPP+]$_{in}$") to determine the membrane potential.

Several researchers reported improvements of the TPP$^+$ selective electrode. Labajova et al. reported the construction of an optimized system for mitochondrial membrane potential measurement based on the TPP$^+$-selective electrode discovered by Kamo. See A. Labajova, A. Vojtiskova, P. Krivakova, J. Kofranek, Z. Drahota and J. Houstek, Evaluation of mitochondrial membrane potential using a computerized device with a tetraphenylphosphonium-selective electrode, *Anal. Biochem.*, 2006, 353, 37-42. Their device consisted of a measuring chamber with a maximum volume of 5 mL, reference electrode, TPP$^+$-selective electrode, personal computer, and MATLAB/Simulink software that provided signal acquisition, processing, and display. Satake et al. reported a coated wire electrode that was sensitive to TPP$^+$. Satake et al., *Analytical Letters*, 24(2), 295-304 (1991). Their device employed TPP$^+$ tetraphenylborate as the ion sensor and was demonstrated to have a linear response for concentrations within 1 mM to 30 μM.

Current technology requires several hundred milligrams of isolated mitochondria for functional assays to determine $\Delta\Psi_m$. It is desirable, however, to have a functional assay that can operate with a much smaller sample of mitochondria. Because of very limited sample availability, technology advances that require reduced sample size (preferably, many orders of magnitude) will dramatically enable and/or facilitate the evaluation of mitochondrial function in clinical biopsy samples and certain cell lines.

SUMMARY

In a first embodiment, a microfluidic sensor device includes a substrate having disposed thereon a reference electrode and a working electrode, wherein the reference electrode is disposed in a first solution holding region and wherein the reference electrode is disposed in a second solution holding region separate from the first solution holding region. The microfluidic sensor device includes a sample chamber configured to hold a sample, the sample chamber separated from the first solution holding region by a polyvinyl chloride (PVC) protective member, the sample chamber separated from the second solution holding region by a TPP$^+$ ion selective membrane.

In another embodiment, a method of making a microfluidic sensor device includes patterning a working electrode and a separate reference electrode on a substrate; applying a first layer of PDMS over the substrate so as to define respective openings over the working electrode and the reference electrode; applying a TPP membrane to the first layer of PDMS over the opening of the working electrode; applying a PVC membrane to the first layer of PDMS over the opening of the reference electrode; applying a second layer of PDMS over the first layer of PDMS so as to define respective openings over the TPP membrane and the PVC membrane; and applying a third layer of PDMS over the second layer of PDMS, the third layer of PDMS having openings corresponding to the openings in the second layer of PDMS.

In another embodiment, a microfluidic sensor device includes a substrate having patterned thereon at least one Ag/AgCl electrode (working electrode) and an inner chamber overlying the at least one Ag/AgCl electrode. The device includes an ion selective permeable membrane permeable to TPP$^+$ disposed on one side of the first chamber and a sensing chamber overlying the ion selective permeable membrane. A separate reference electrode is inserted into the sensing chamber. The working electrode and reference electrode are coupled to a voltmeter to measure voltage. This voltage can then be translated into a TPP$^+$ concentration which is used to the mitochondrial membrane potential ($\Delta\Psi_m$).

A method of making a microfluidic sensor device includes patterning a plurality of contact electrodes on a substrate at different test regions; forming a silver/silver chloride electrode at each test region, the silver/silver chloride electrode electrically connected to at least one contact electrode; forming a first PDMS layer comprising a plurality of microfluidic channels containing a hole therein; applying the first PDMS layer to the substrate so that the silver/silver chloride electrodes are surrounded by the holes in the first PDMS layer; applying TPP$^+$ selective membranes to the first PDMS layer over each hole; and applying second and third PDMS layers over the first PDMS layer, wherein the second and third PDMS layers have respective holes corresponding to the locations of the holes in the first PDMS layer.

In another aspect of the invention, a method for analyzing mitochondrial bioenergetics includes providing a microfluidic device having first chamber containing an electrode therein and a second chamber separated from the first chamber by a ion selective membrane; loading the second chamber with a sample containing mitochondria; measuring the voltage using the electrode; and determining the membrane potential based at least in part on the measured voltage.

In another aspect of the invention, a method of for analyzing mitochondrial bioenergetics includes providing a microfluidic device having at least one chamber therein with a volume between 0 µl and about 100 µl. The at least one chamber is loaded with a sample containing mitochondria and the mitochondrial membrane potential $\Delta\Psi$m of the sample is measured.

BRIEF DESCRIPTION OF THE DRAWINGS

FIGS. 13A-13F illustrate a process of making the device according to the second embodiment.

DETAILED DESCRIPTION OF THE ILLUSTRATED EMBODIMENTS $\Delta\Psi$m drives the conversion of ADP to ATP by utilizing the proton electrochemical proton motive force ($\Delta$p), that is generated by serial reduction of electrons through the respiratory electron transport chain. The proton motive force generated by the oxidation steps of the electron transport chain subsequently drives the proper functioning of the mitochondria. The relationship between the proton motive force $\Delta$p and the mitochondrial membrane potential $\Delta\Psi$m is given by Equation 2 below.

$$\Delta p = \Delta\Psi_m - [2.3(RT/F)]\Delta pH, \qquad (2)$$

where R is the universal gas constant (R=8.314472 J/K mol), T the absolute temperature, and F the Faraday constant (F=96485.3 C/mol). $\Delta$p depends on both the electrical difference across the inner membrane ($\Delta\Psi_m$) and the pH difference ($\Delta$pH) between the matrix and inner membrane space. The contribution of $\Delta\Psi_m$ to the overall value of $\Delta$p is much larger than that of the pH changes because of the high buffering capacity in the mitochondria. Here, the device designs focuses on $\Delta\Psi$m as a valid indicator of $\Delta$p and, thus, the overall metabolic status of the mitochondria.

Figure 1:
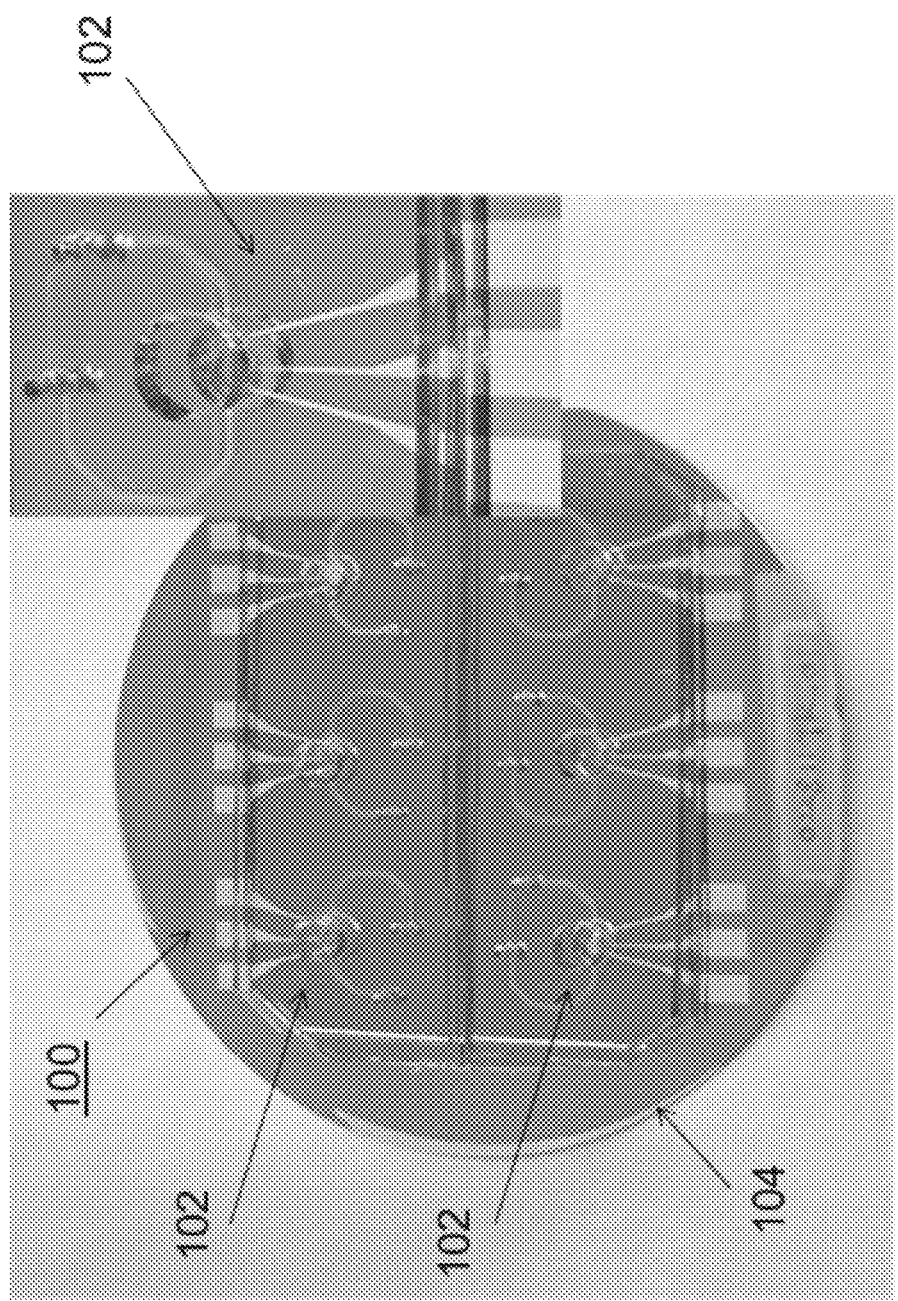
FIG. 1 illustrates a photographic image of a sensor device according to one embodiment.

In a first embodiment, as seen in FIG. 1, a microfluidic TPP+ selective sensor 100 is provided. In this embodiment, the TPP+ selective sensor 100 contains a plurality of test regions 102 disposed on a single substrate 104. Inset in FIG. 1 is a magnified view of a single test region 102. In this regard, the selective sensor 100 may be multiplexed with multiple measurements made on a single platform. In one aspect, the test regions 102 may be formed atop a substrate 104 formed form silicon, glass, or quartz.

Figure 2:
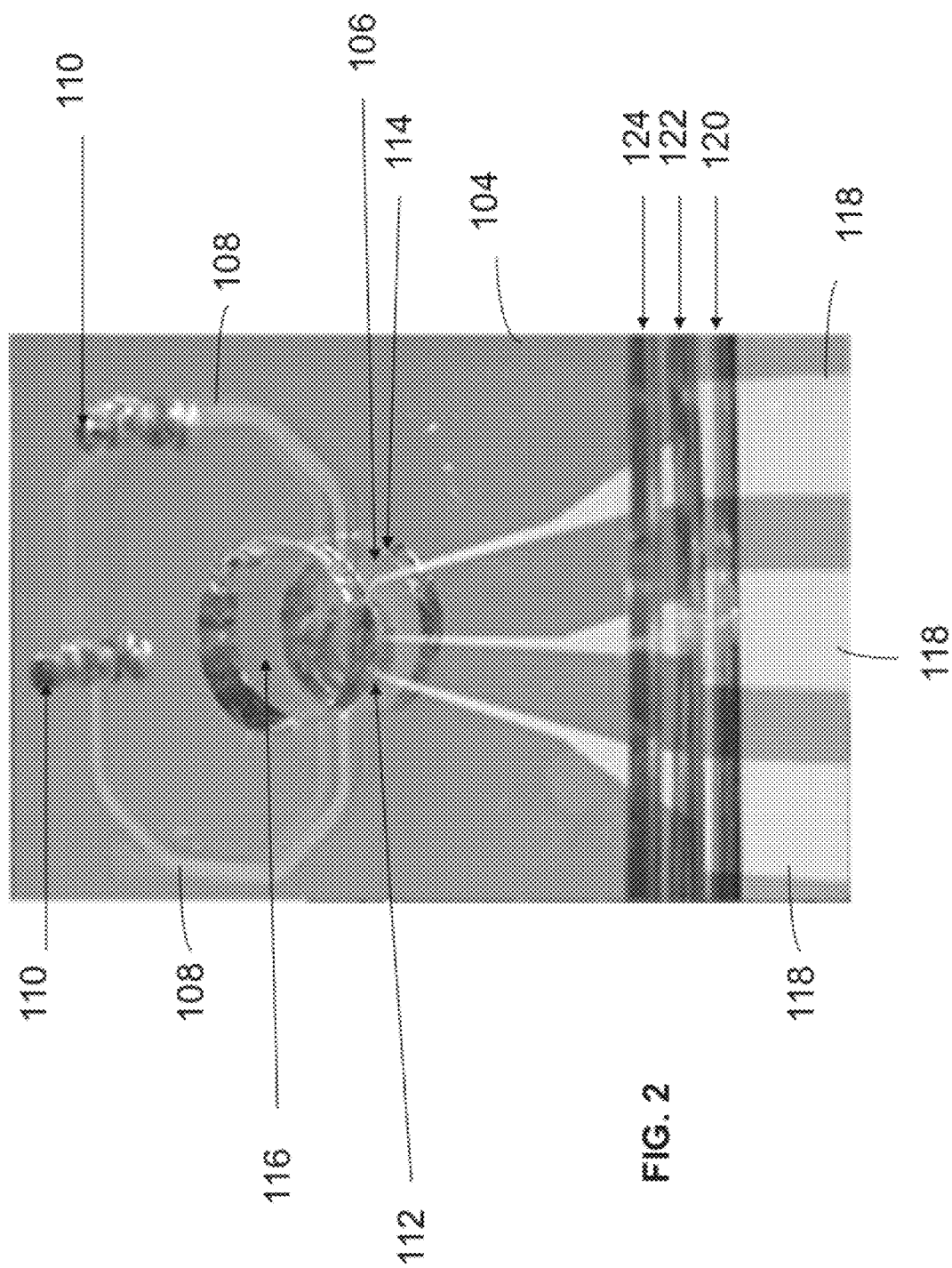
FIG. 2 illustrates a magnified view of a portion of the sensor device of FIG. 1.

FIG. 2 illustrates a photograph of a single test region 102 that forms the TPP+ selective sensor 100. The single test region 102 has an inner chamber 106 that sits on top of the substrate 104 which, as described above, may include a silicon wafer. As explained below, the inner chamber 106 is formed in a PDMS layer that is disposed atop the substrate 104. Alternative substrates 104 include, by way of example, glass or quartz wafers. The inner chamber 106 defines a volume defined by a hole or void in the PDMS layer and is connected with microfluidic channels 108. The microfluidic channels 108 (two of which are illustrated in FIG. 2) connect at one respective end to the inner chamber 106 and at an opposing end to access holes 110. During use, fluid may be injected into the microfluidic channels 108 through the access holes 110. The access holes 110 may also function as ventilation holes that are connected to the microfluidic channels 108 and the inner chamber 106.

A silver/silver chloride electrode 112 disposed in the inner chamber 106. Typically, the silver/silver chloride electrode 112 is located on region of the substrate 104 surrounded by the inner chamber 106. Thus, the silver/silver chloride electrode 112 is exposed to the contents of the inner chamber 106. An ion selective permeable membrane 114 is disposed atop the inner chamber 106. In this regard, the inner chamber 106 is defined by a volume formed in the PDMS layer between the ion selective permeable membrane 114 and the silver/silver chloride electrode 112 disposed on the substrate 104. The ion selective permeable membrane 114 allows tetraphenylphosphonium ($TPP^+$) ions to cross through the membrane while the same time the ion selective permeable membrane 114 seals the inner chamber 106 from a separate sensing chamber 116.

Still referring to FIG. 2, silver contact electrodes 118 are patterned on top of the substrate 104 and electrically connected to the silver/silver chloride electrode 112 that is contained in the inner chamber 106. The silver/silver chloride electrode 112 is patterned on top of the substrate 104. As seen in FIG. 2, the microfluidic features are disposed in one or more PDMS layers that are disposed atop the substrate 104. FIG. 2 illustrates three (3) such PDMS layers. A first PDMS layer 120 disposed atop the substrate 104 contains the microfluidic channels 108 and the inner chamber 106. The second PDMS layer 122 and third PDMS layer 124 each have three holes punched out of each respective layer. This is such that when second and third PDMS layers 122, 124 are overlaid on top of the first PDMS layer 120, two of the three holes align with the access holes 110 of the first PDMS layer 120 and the third hole forms the sensing chamber 116 that is in contact with the ion selective membrane 114.

Figure 3:
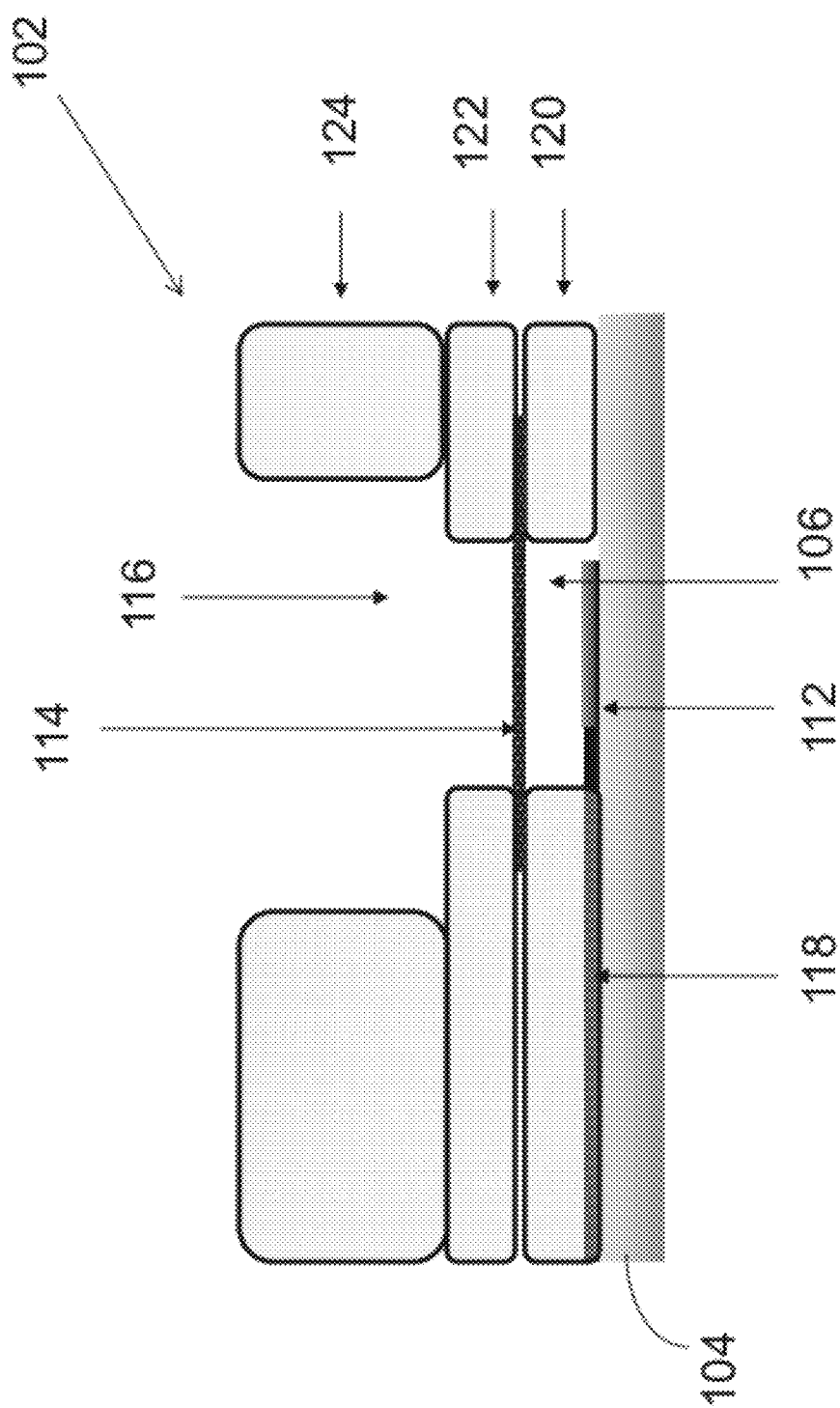
FIG. 3 is a side view of a single test region of the type contained in the sensor device of FIGS. 1 and 2.

FIG. 3 illustrates a side view of a single test region 102 of the sensor 100. FIG. 3 illustrates the substrate 104 as well as the silver/silver chloride electrode 112 and the silver contact electrode 118. The silver/silver chloride electrode 112 is illustrated being disposed in the inner chamber 106. The ion selective membrane 114 is disposed above the inner chamber 106 and is partially sandwiched between first PDMS layer 120 and the second PDMS layer 122. The ion selective membrane 114 separates the inner chamber 106 from the upper (in the context of FIG. 2) sensing chamber 116. Additional volume is provided to the sensing chamber 116 by using the third PDMS layer 124 which has an aperture formed therein. This aperture provides a portion of the volume for the sensing chamber 116 together with the aperture formed in the second PDMS layer 122. While FIG. 3 illustrates a single test region 102 it should be understood that multiple test regions 102 like that illustrated in FIG. 3 can be provided on a single substrate 104 as illustrated in FIG. 1

In one aspect of the sensor 100, very small quantities of mitochondria are needed for determining mitochondrial membrane potential. Specifically, the device illustrated in FIGS. 1-3 may determine mitochondrial membrane potential using only nanogram-quantities of mitochondria. In one aspect, the sensor 100 measures the changes in $TPP^+$ concentration in the sensing chamber 116 as various substrates key to mitochondrial metabolism are added into the sensing chamber 116 of the microfluidic device.

Figure 4:
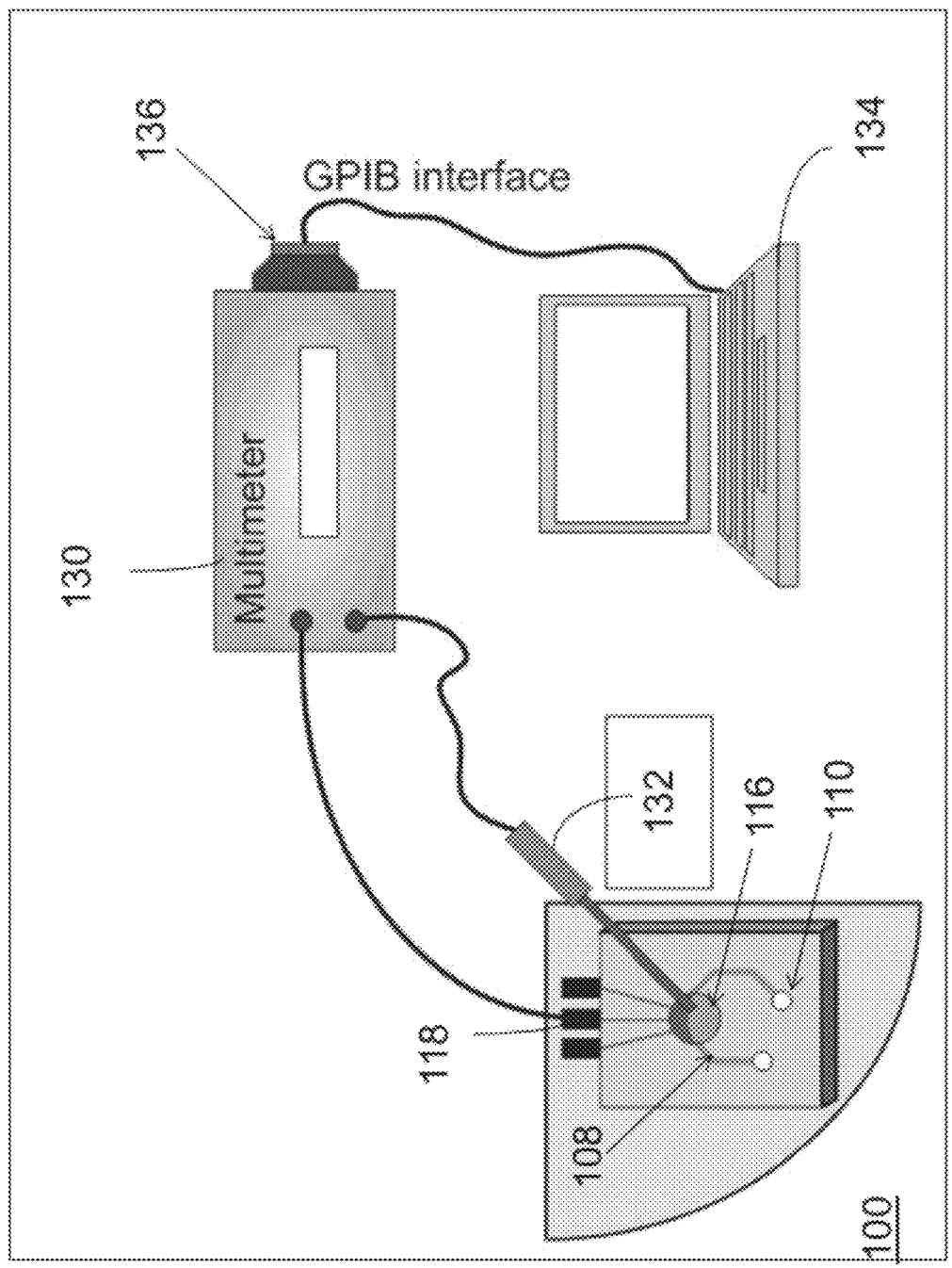
FIG. 4 illustrates a system for measuring mitochondrial membrane potential according to one embodiment.

Turning now to the operation and use of the sensor 100, in one preferred embodiment, the inner chamber 106 is filled with a $TPP^+$ solution that is injected or otherwise loaded into the inner chamber 106 through the access holes 110 by using a micropipette. Of course, other loading devices may be used such as a syringe or the like. The $TPP^+$ solution is left in the sensor 100 for about twelve (12) hours. FIG. 4 illustrates a method of measuring $TPP^+$ concentration. During the measurement of the mitochondrial membrane potential, $TPP^+$ solution is injected into the inner chamber 106, the silver contact electrode 118 of the sensor 100 is connected to a voltmeter 130 (or multimeter) that reads the $TPP^+$ concentration in the sensing chamber 116 through the measurements taken by the silver/silver chloride electrode 112. A separate reference electrode 132, such as a commercial, leakage-free Ag/AgCl reference electrode (Warner Instruments), is coupled to the voltmeter 130 and is inserted into the sensing chamber 116 to measure the $TPP^+$ concentration. The voltmeter 130 is connected to a computer 134 via GPIB interface 136 that records the voltages read by the voltmeter 130, the recorded time trace (or background noise) is later used to calculate the mitochondrial membrane potential with software (e.g., IGOR PRO software available from WaveMetrics (www.wavemetrics.com)). Of course, the computer 134 may be loaded with other software that can be used to calculate mitochondrial membrane potential as described herein.

Filling the inner chamber 106 with $TPP^+$ primes the sensor 100 for use in order to activate the $TPP^+$ ion selective membrane 114. The inner filling solution is replaced (10 mM $TPP^+$ solution) after priming and no air pockets should form when the inner filling solution is replaced since air pockets would create an open circuit against the ion selective membrane 114 and signal-reading errors.

Calibration of the sensor 100 has been conducted on the sensor 100 to ensure that measurements can be reproducible even after multiple measurements have been made. For calibration, the sensing chamber 116 was rinsed with deionized water and respiration buffer before filling with fresh respiration buffer or 100 mM NaCl for calibrations. The sensor 100 was characterized using a 5-point calibration curve with $TPP^+$ concentrations ranging from 0.3 µM to 600 µM conducted in both respiration buffer and NaCl solutions. The potential difference between the reference electrode 132 and the silver/silver chloride electrode 112 (e.g., working electrode) was monitored while incrementally increasing the $TPP^+$ concentrations within the sensing chamber 116.

Figure 5:
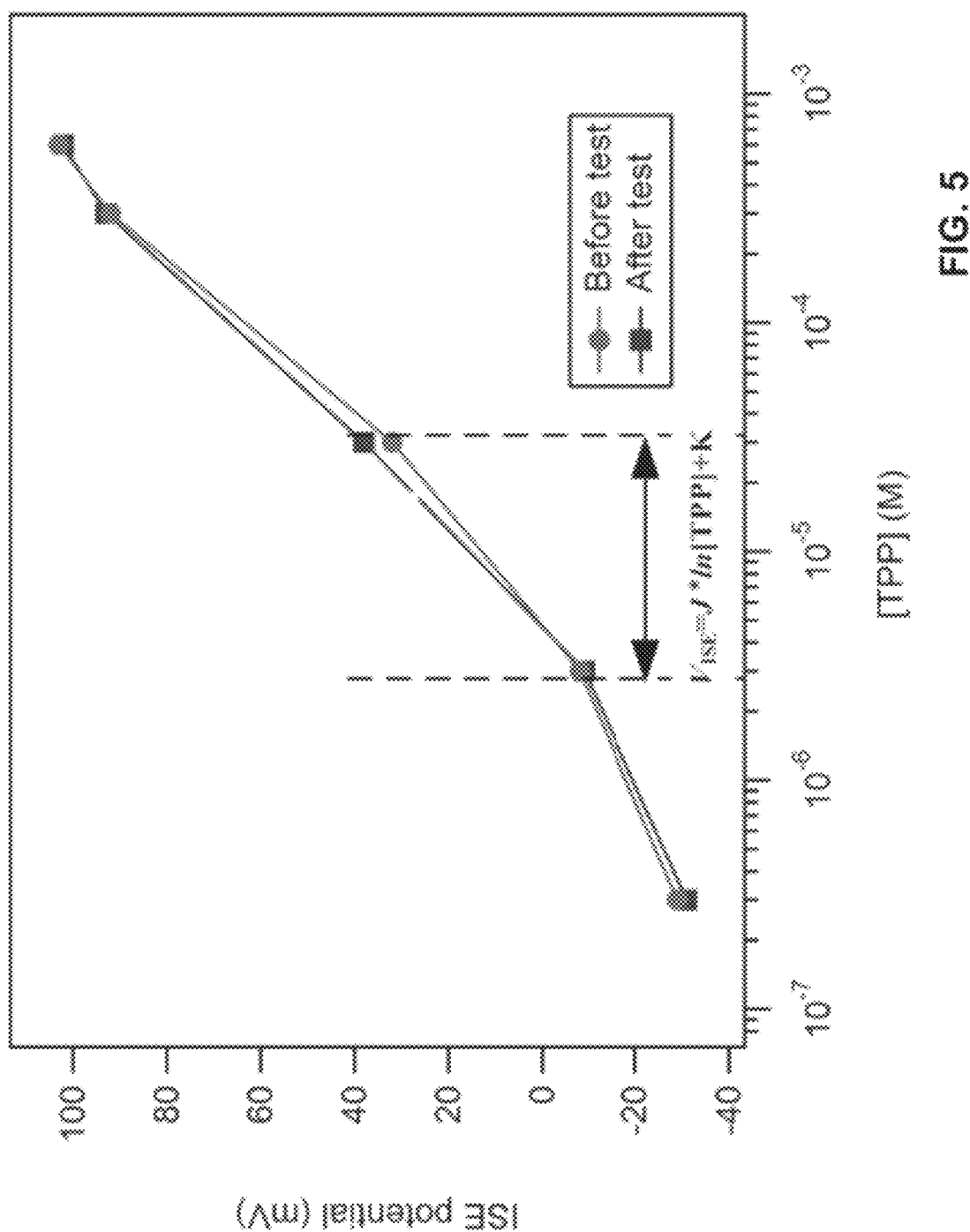
FIG. 5 illustrates a calibration curve for a sensor device for multiple tests.
Figure 6:
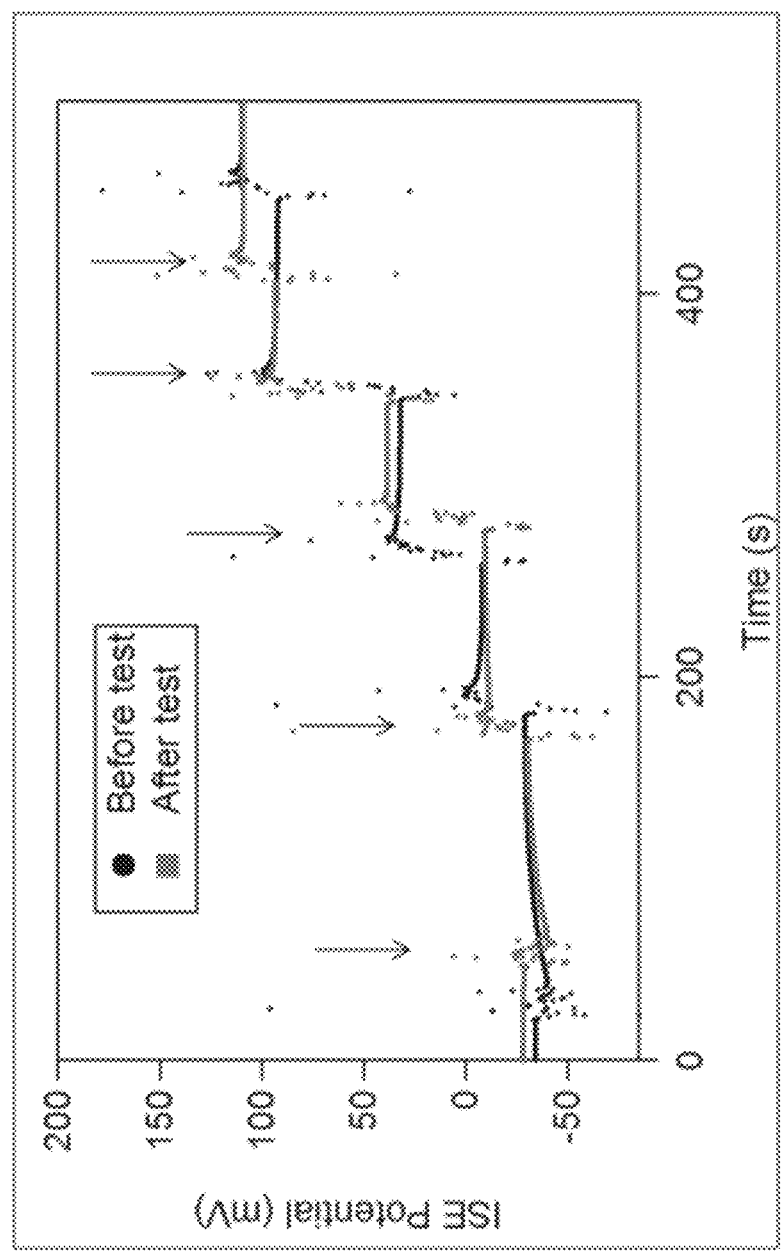
FIG. 6 illustrates a graph of ISE potential (mV) as a function of time. Arrows reflect the addition of TPP$^+$.

FIG. 5 illustrates two calibration curves (ISE potential vs. $TPP^+$ concentration) measured before and after a typical mitochondrial measurement and demonstrates the reproducibility, durability, and small drift of the sensor 100 between experiments. FIG. 6 illustrates a graph of ISE potential as a function of time. FIG. 6 shows the signal stabilizing just a few seconds following each successive addition of $TPP^+$ (arrows) and this data was subsequently used for the calibration curves.

The user may obtain isolated mitochondria from known protocols. For example, analysis of mitochondrial membrane potential was carried out with isolated human mitochondria (Heb7A). Heb7A is a HeLa cell-derived line which is commonly used for analytical study in research labs for their unique growth and molecular characteristics. These adherent cells were maintained in log growth phase and cultured in media consisting of MEM-e (Gibco, 11090) supplemented with 10% FCS (Hyclone, SH30072.03), 2 mM L-glutamine (Gibco, 25030), and NEAA (Gibco, 11140). The mitochondrial isolation protocol was modified from Trounce et al. See I. A. Trounce, Y. L. Kim, A. S. Jun, and D. C. Wallace, "Assessment of mitochondrial oxidative phosphorylation in patient muscle biopsies, lymphoblasts, and transmitochondrial cell lines," Methods Enzymol, vol. 264, pp. 484-509, 1996. Approximately $10^7$ cells were pelleted and washed in PBS (phosphate buffered saline). Ice-cold H-buffer (210 mM mannitol, 70 mM sucrose, 1 mM EGTA, 5 mM HEPES, 0.5% BSA) was used for all of the subsequent steps of mitochondrial isolation. The cells were physically sheared with 15-20 passes in a cold Dounce homogenizer and centrifuged at low speed (800×g for 5 min) at 4° C. in an Eppendorf 5417R centrifuge. The cell lysate suspension was incrementally clarified to remove the large cell debris through four rounds of low speed spins and the mitochondria were then pelleted with two rounds of high speed spins (10000×g for 20 min). An aliquot was washed in BSA-free H-buffer for protein determination using the BCA Protein Assay Kit (Thermo Scientific, Prod#23227). The isolated mitochondrial sample was diluted in ice-cold respiration buffer for immediate analysis. Once the device is calibrated, isolated mitochondria are added into the sensing chamber 116.

Upon introduction of mitochondria into the sensing chamber 116, mitochondria quickly absorbs $TPP^+$ according to their $\Delta\Psi m$ leading to decrease in concentration of $TPP^+$ in the sensing chamber 116. In addition to the uptake of $TPP^+$ by the mitochondria, the $TPP^+$ concentration in the sensing chamber 116 is also decreased by dilution when the solution of mitochondria are added into the sensing chamber 116.

The mitochondrial membrane potential may be calculated with the following using the following equation:

$$\Delta\Psi_m = \frac{RT}{F}\ln\frac{V_0[TPP^+]_0/[TPP^+]_t - V_t - K_0 P}{V_m P + K_i P} \quad (3)$$

In Equation 3, $[TPP^+]_o$ and $[TPP^+]_t$ represent $TPP^+$ concentration in the sensing chamber 116 before the addition of mitochondria and at time t respectively. $V_o$ is the initial buffer volume in the sensing chamber 116 and $V_t$ represents the final volume in the chamber which includes the total mass (in mg) of mitochondrial protein (P) added in the assay. For our purposes, the mitochondrial matrix volume ($V_m$) was assumed to be equal to 1 μL/mg protein. The partition coefficients describe the innate binding and accumulation of the $TPP^+$ ion to the matrix ($K_i$) and external ($K_o$) faces of the inner membrane and are given values of 7.9 μL/mg and 14.3 μL/mg, respectively.

Figure 7:
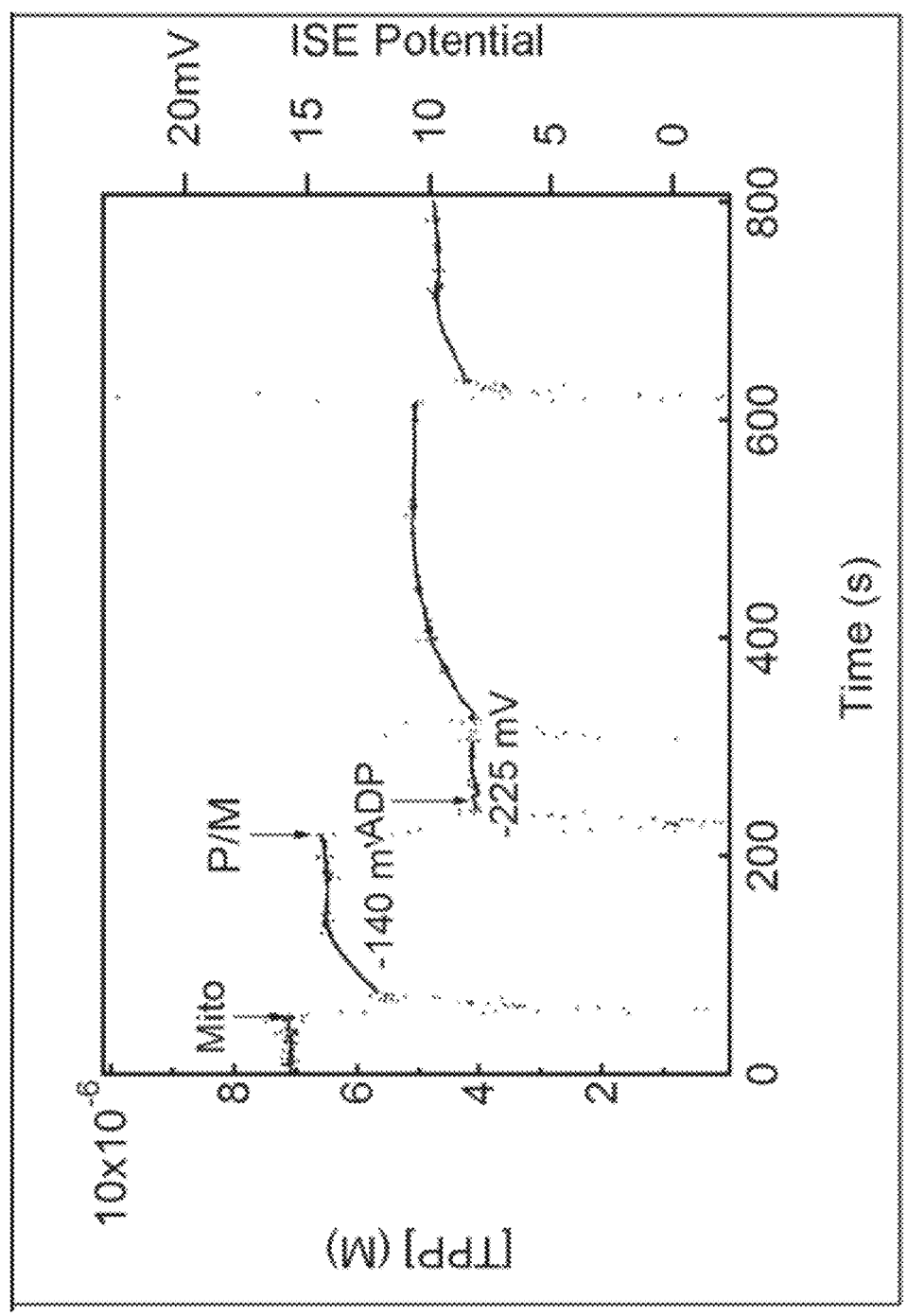
FIG. 7 illustrates a graph of TPP$^+$ concentration as a function of time.

Specifically, in one working example of the sensor 100, the initial concentration of $TPP^+$ in the sensing chamber 116 was 7.2 μM and the initial volume of the solution is 70.5 μL. FIG. 7 illustrates the $TPP^+$ concentration as a function of time. In FIG. 7, it can be seen at t=50 seconds that when the mitochondria are initially added to the sensing chamber 116, after the time trace stabilizes, the ion selective electrode measures the $TPP^+$ concentration at 6.55 μM. The addition of the mitochondria in solution increases the volume to 75.5 μL. These numbers are inputted into Equation 3 above and the $\Delta\Psi m$ is calculated to be 140 mV.

Before pyruvate and malate are added to the sensing chamber at t=220 seconds, the initial $TPP^+$ concentration is at 6.55 μM and the initial volume is 75.5 μL. After pyruvate and malate is added to the device, the $TPP^+$ concentration is 4.11 μM and the final volume of the sensing chamber is 80.5 μL. When these values are inputted into Equation 3, the mitochondrial membrane potential is 225 mV as shown in FIG. 7.

Figure 8:
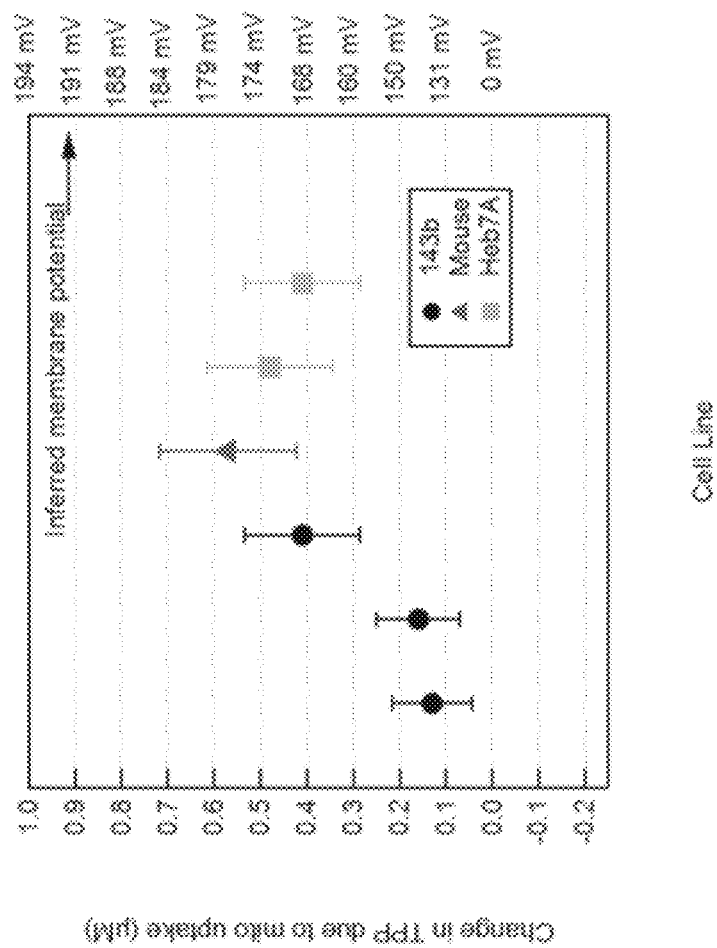
FIG. 8 illustrates a graph of change in TPP$^+$ due to mitochondria uptake for various cell types.

The same series of measurements with mitochondria from Heb7A and mouse muscle cell lines were performed and compared on the device. The decrease in $TPP^+$ concentration after addition of mitochondria, and the corresponding $\Delta\Psi_m$ values are plotted in FIG. 8 which were obtained from 6 different assays of mitochondria. As expected from prior studies of mitochondrial bioenergetics, $\Delta\Psi_m$ of mitochondria from mouse skeletal muscle showed the largest $\Delta\Psi_m$ value among other cell lines indicating the vibrant activity of the skeletal muscle tissue. The membrane potential of Heb7A was slightly higher than that of 143b as shown on FIG. 8. Overall the results of the mitochondrial assays using the device disclosed in this application were consistent with the results of prior studies.

It should be understood that the mitochondrial membrane potential may be calculated either manually using Equation 3 above or, alternatively, automatically using a computer 134 loaded with software. The software may use a series of ISE potential measurements to calculate the concentration of $TPP^+$. For example, ISE potential measurements along with a calibration curve generated for the sensor 100 can be used to measure the concentration of $TPP^+$. These values can then be input into Equation 3 along with volume measurements. For instance, volume changes may be input manually to the computer or they may be automatically input if, for example, the computer 134 is associated with an automatic pipetting system (or other dispensing system) capable of determining volume additions.

Figure 9C:
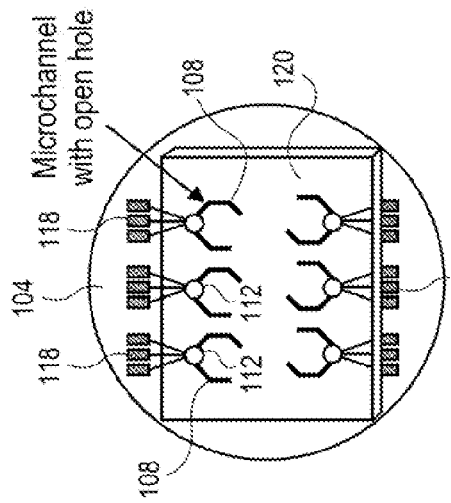
FIGS. 9A-9D illustrate a process of making a sensor device according to one embodiment.
Figure 9B:
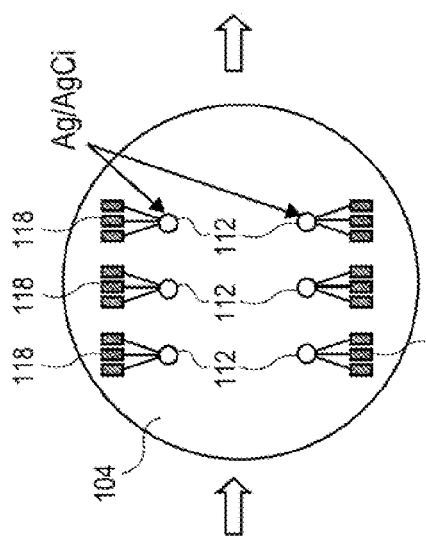
Figure 9A:
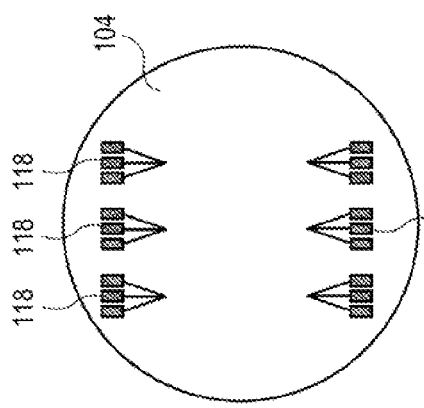

The microfabrication process of the sensor device of FIGS. 1-3 is schematically illustrated in FIGS. 9A-9D. With reference to FIG. 9A, a substrate 104 such as a silicon wafer was used as the device substrate to allow compatibility with standard semiconductor wafer-scale microfabrication technologies. Thin films of titanium (Ti) (50 nm) and silver (Ag) (1.5 μm) were deposited onto the silicon wafer by electron beam physical vapor deposition as shown in FIG. 9A to form contact electrodes 118. The silver film was lithographically patterned on top of the Ti film into electrodes using Shipley 1827 photoresist. Wet etching was carried out using a silver etchant made of 1:1 mixture of nitric acid and DI water followed by Ti etching.

The portion of the silver electrodes that will be situated in the inner chambers 106 were chlorinated chemically by dropping 50 μl of 0.1 M $FeCl_3$ solutions onto the electrode to create Ag/AgCl electrodes as seen in FIG. 9B. Three layers of silicone rubber (PDMS) were prepared separately by soft lithography. The first layer 120 has a microfluidic channel 108 with a width of 400 μm and a 50 μm depth to contain the 10 mM $TPP^+$ inner filling solution needed for the ion selective sensing. These microfluidic channels 108 were produced by soft lithography with a thick negative photo resist (SU-8) mold to keep the volume of the inner filling solution constant. A 2 mm hole was drilled through the center of the microfluidic channel 108 of the first PDMS layer 120 to provide an interface between the inner filling solution and the medium in the sensing chamber through the ion selective membrane. The $TPP^+$ ion selective (IS) membrane solution was prepared with a mixture of tetrahydrofuran (THF) and dioctyl phthalate, polyvinyl chloride (PVC), and tetraphenylboron ($Na^+TBP^-$). FIG. 9C illustrates assembly of the first PDMS layer 120 with the microfluidic channels 108 as well as a aperture overlying the Ag/AgCl electrode 112.

Figure 9D:
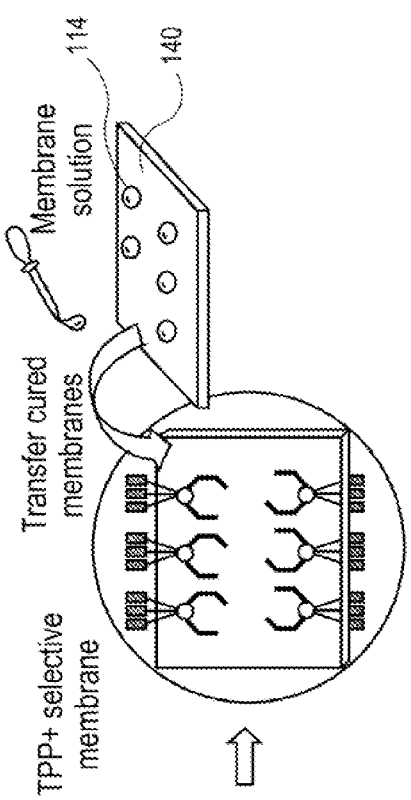

The IS membranes 114 are first prepared and cured on a separate PDMS scaffold 140 before being positioned and deposited on the chip as illustrated in FIG. 9D. As depicted in FIG. 9D, a clean 2 mm thick PDMS scaffold 140 was first aligned on top of the first PDMS layer 120, so that the open 2 mm center holes of six microfluidic channels are visible from above. 30 μL of freshly prepared ion selective membrane solution was then carefully spotted onto this PDMS scaffold 140 to correspond to the position of the channel holes underneath. These TPP$^+$ ion selective (IS) membranes 114 were allowed to cure overnight at room temperature. The following day, the scaffold 140 with the TPP$^+$ ion selective (IS) membranes 114 was flipped over (shown by arrow in FIG. 9D), positioned so that the cured IS membranes 114 cover the TPP$^+$ solution chamber, and the TPP$^+$ ion selective (IS) membranes 114 are gently pressed out of the scaffold 140 and onto the first PDMS layer 120. Portions of the second PDMS layer 122 and third PDMS layer 124 that are to be overlaid on top of the first PDMS layer 120 and three holes in the second and third layer of PDMS are removed so that the sensing well 116 and access holes 110 are formed when these two PDMS layers 122, 124 are aligned and assembled on top of the first PDMS layer 120.

The process depicted in FIGS. 9A-9D illustrates the formation of six test regions 102 as part of the sensor 100. The test regions 102 are formed on a single four (4) inch Silicon wafer. It should be understood, however, that more or less test regions 102 could be formed on a single substrate 104. Likewise, the Silicon wafer used for the substrate 104 may be smaller or larger. The sensor device 100 produced by the process of FIGS. 9A-9D enables scalable test sites to be integrated into a standard silicon wafer. The sensor device 100 advantageously requires small protein quantities—quantities that are four orders of magnitude less than current assays. For example, the concentration of isolated mitochondria used in membrane potential measurements may have a concentration below 1 ng μL$^{-1}$. In one aspect, the concentration may be around 0.3 ng μL$^{-1}$ which is four orders of magnitude smaller than concentrations used in conventional assays 3 μg μL$^{-1}$.

Figures 10A, 10B:
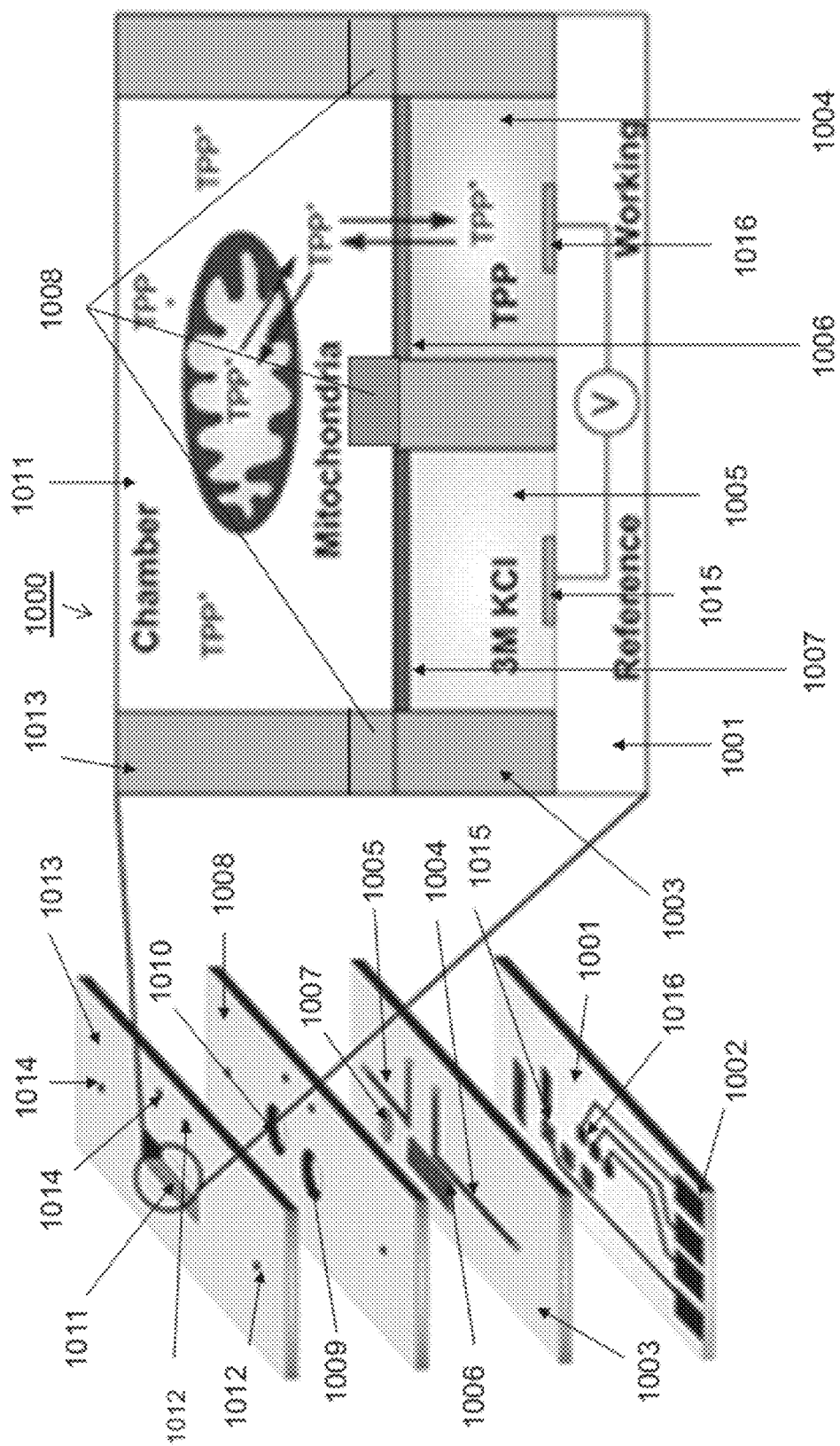
FIG. 10A illustrates a perspective view of layers making up a sensor device according to another embodiment.
FIG. 10B illustrates a side view of the sensor device of FIG. 10A.

Another embodiment of a sensor device 1000 is illustrated in FIGS. 10A and 10B. Unlike the embodiment of the device shown in FIGS. 1-3, this embodiment of the sensor device 1000 has an internal reference electrode built into the device. FIG. 10A is a view of each of the various layers that form the device. FIG. 10B is a side view of the sensor device 100 showing the various layers and components. As seen in FIGS. 10A and 10B, the sensor device 1000 sits on top of a glass substrate 1001 and silver/silver chloride electrodes 1002 are patterned on top of the glass substrate 1001. A first PDMS layer 1003 is disposed atop the substrate 1001 with "L" shaped channels 1004 and 1005 cut out of the first PDMS layer 1003. As shown in FIG. 10B, the "L" shaped channel 1004 forms the working electrode chamber containing inner TPP$^+$ ion solution and the working electrode 1016 detects the TPP$^+$ concentration. The "L" shaped channel 1005 forms the reference electrode 1015 containing an inner KCl solution. An ion selective membrane 1006 such as TPP membrane seals off the "L" shaped channel 1004 from the second and third PDMS layers 1008 and 1013. A protective membrane 1007 seals off the "L" shaped channel 1005 from the second and third PDMS layers 1008 and 1013. The protective membrane 1007 may be made of polyvinyl chloride although other materials may be used. Two large holes 1009 and 1010 are cut out of the second PDMS layer 1008. Four additional smaller holes are cut out of the second PDMS layer 1008 and these holes will serve as access holes to the "L" channels 1004 and 1005. A rectangle is cut out of the third PDMS layer 1013 and this rectangle removed from the third PDMS layer is used to define the sensing chamber 1011. Also cut out of the third PDMS layer are four small holes 1012, 1014 and when overlaid on top of the second PDMS layer allows for fluid to be injected into the "L" shaped channels 1004 and 1005.

During use of the sensor device 1000, the "L" channel 1004 is filled with a TPP+ solution that is injected into "L" channel 1004 through the access holes 1012 by using a syringe. Either access holes 1012 and 1014 may serve as vents. The TPP+ selective electrode 1016 is soaked in 10 mM TPP$^+$Cl$^-$ solution overnight before calibration and the reference electrode 1015 was conditioned in 3 M KCl solution.

The TPP+ selective working electrode 1016 and Ag/AgCl reference electrode 1015 were connected to the positive and negative input of a voltmeter (Agilent 34401A digital multimeter). The voltmeter was linked to the computer via a GPIB interface (National Instrument, GPIB-USB-HS) for data communication. The voltage signal from the voltmeter was acquired using Labview software, so that simultaneous monitoring of the mitochondrial membrane potential could be achieved.

The sensor calibration was performed by adding various concentrations of TPP$^+$Cl$^-$ solution ranging from 10 μM to 10 mM in both respiratory buffer and 0.1 M NaCl solutions at 25° C. to the sensing chamber 1011 while monitoring potential differences between working electrode and reference electrodes.

The evaluation of the mitochondrial membrane potential was performed with human mitochondria (Heb7A) in respiration buffer (225 mM mannitol, 75 mM sucrose, 10 mM KCl, 10 mM Tris-HCl, 5 mM KH$_2$PO$_4$, pH 7.2). The measurements were repeated 4 times with freshly prepared mitochondria to confirm the performance and the reproducibility of the sensor. The results of the measurements showed reproducible responses under similar conditions. 25 ng of isolated mitochondria in 85 μL was used for the test resulting in a final concentration of 0.29 ng/μL. The mitochondrial membrane potential ($\Delta\Psi m$) can be determined using Equation 3 as already demonstrated in this application.

Figure 11:
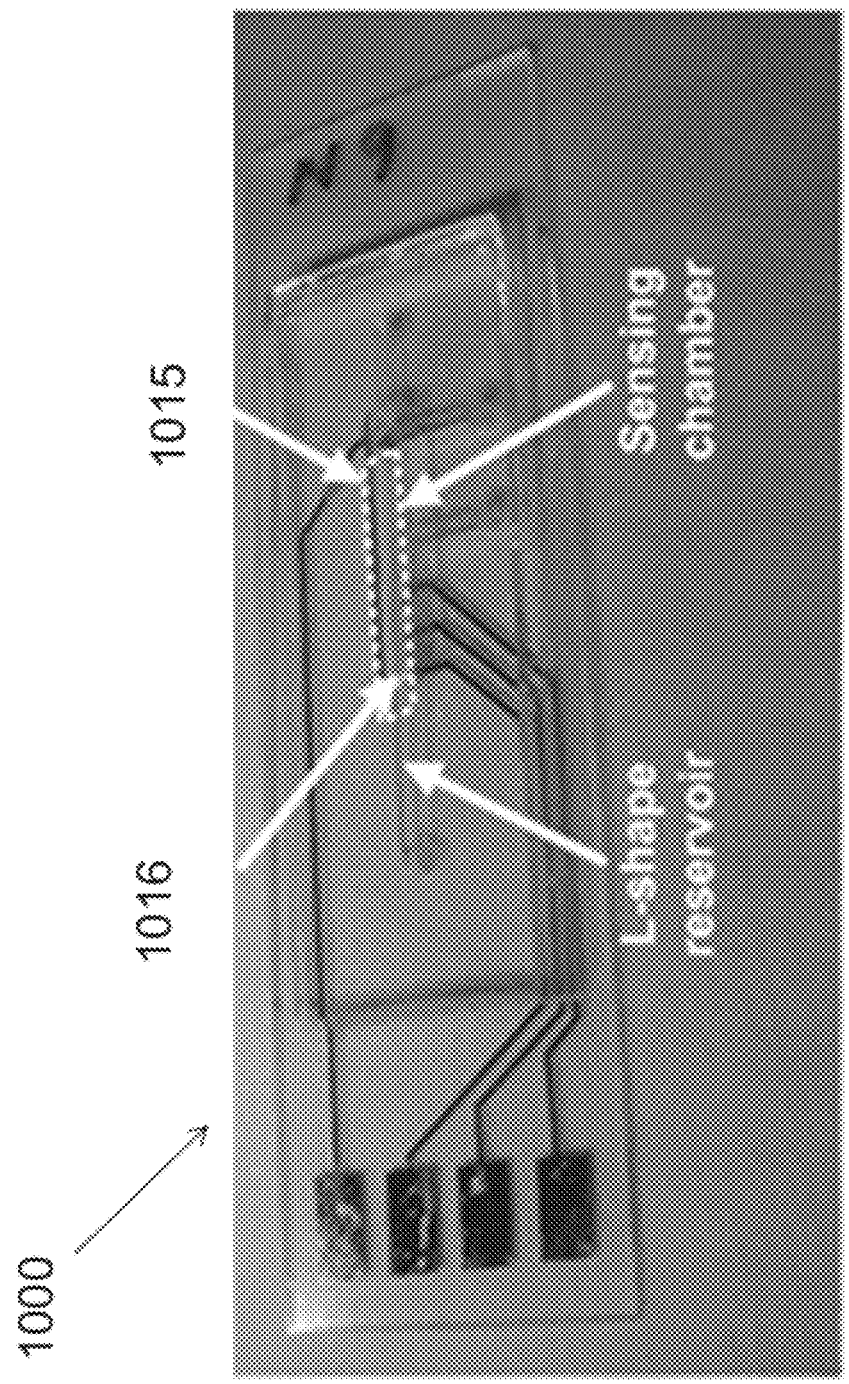
FIG. 11 is a photographic image of the sensor device according to this alternative embodiment.
Figure 12:
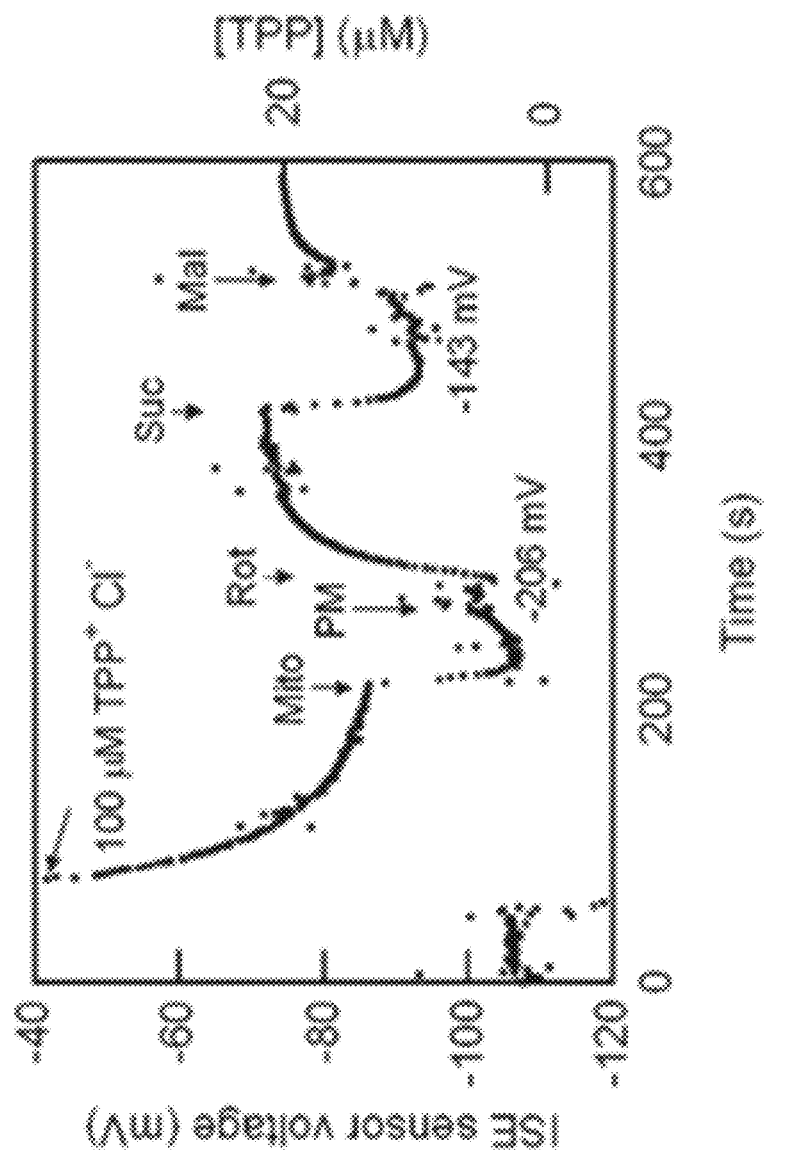
FIG. 12 illustrates the mitochondrial membrane potential measured by the second embodiment of the sensor device.

FIG. 11 illustrates an image of a complete sensor device 1000 showing the reference electrode 1015 and working electrode 1016 with arrows. The results of a typical assay using the sensor device 1000 are shown in FIG. 12. The sensing chamber was filled with an initial volume of 71 μL respiration buffer. Once the plot baselined to zero, a 100 μM TPP$^+$Cl$^-$ solution was added to provide a working concentration. The working concentration of TPP$^+$ was kept at about 10 μM to prevent inhibition of respiration. After stabilization, isolated mitochondria (5 ng μL/1) were added to the sensing chamber 1011. The fresh mitochondria quickly took in TPP$^+$ from the chamber defined by the "L" shaped channel 1004 due to its value of $\Delta\Psi m$, resulting in a lower TPP$^+$ concentration in the chamber as measured by the ion selective electrode. However, as the mitochondria consumed substrates in the respiration buffer, the substrate concentration became depleted, and the magnitude of $\Delta\Psi m$ began to decrease slowly as a result, causing a slow increase in TPP$^+$ in the sensing chamber.

This decrease in the magnitude of $\Delta\Psi m$ was temporarily halted by the addition of complex I substrate pyruvate and malate ("P/M" as shown on FIG. 12), which allowed the mitochondria to increase the magnitude of $\Delta\Psi m$ through consumption of these substrates. While there are transients in the data, the slow decrease in the magnitude of $\Delta\Psi m$ is clearly halted by the addition of P/M. The complex I inhibitor Rot halts the mitochondrial consumption of P/M, leading again to a slow decline in the magnitude of $\Delta\Psi m$ (hence an increase in the concentration of TPP$^+$.

The addition of complex II substrate succinate ("Suc" on FIG. 12) allows the mitochondria again to increase the magnitude of $\Delta\Psi m$ (hence decreasing the concentration of TPP$^+$).

The addition of complex II inhibitor malonate ("Mal" on FIG. 12) stops the consumption of succinate, causing again a slow decrease in the magnitude of ΔΨm (thus increasing the concentration of TPP$^+$).

The microfluidic TPP+ selective sensor device 1000 was constructed on a microscope cover glass with PDMS layers. The fabrication steps are schematically illustrated in FIGS. 13A-F. Cover glass slides were cleaned in Piranha solution (mixture of sulfuric acid and hydrogen peroxide with the ratio of 7 to 3) overnight followed by organic solvent cleaning. First, a thin film of titanium (30 nm) was deposited as a seed layer and then Pd (50 nm) and Ag (2.5 μm) were deposited on the cleaned glass substrate using an electron-beam evaporator (Airco/Temescal CV-8) (FIG. 13A). Photolithography was performed with positive photoresist (Shipley 1827) for patterning silver electrodes on the glass substrate. Shipley 1827 was spread out by using a spin coater at 3500 rpm for 30 s with 3 μm thickness and soft-baked at 90° C. for 10 min. The spin-coated glass substrate was exposed to UV-light for 30 s at 6 mW cm$^{-2}$. After a post-bake at 120° C. for 3 min, the exposed photoresist was removed in developer (MF-319, Microposit).

Chlorination of silver (for Ag/AgCl electrode formation) was carried out electrochemically or chemically for both the reference and working electrodes (FIG. 13B). The former was performed in 0.1 M HCl solution at a constant current of 5 mA cm$^{-2}$ for 4 min, and for the latter the silver coated glass substrate was dipped into 0.1 M FeCl$_3$ solution for 40 s without current flow. It was found that the electrode chlorinated with the chemical method in 0.1 M FeCl$_3$ solution works best in terms of robustness and surface morphology. For the sensor characterization and test, only the sensor chlorinated by the chemical method was employed through the study.

The PDMS layer was prepared by a mixture of PDMS prepolymer (Sylgard 184, Microchem) and a curing agent at a ratio of 10:1. A 7 g mixture was poured onto a 4" silicon wafer used as a substrate. After curing PDMS in a hot oven at 90° C. for 15 min, the cured PDMS with thickness of 1 mm was cut into the size of a cover glass and stripped out from the wafer. With a surgical blade and a flat-end needle, two "L" shaped inner filing solution reservoirs were cut in accordance with electrode sensing areas on the glass substrate. For the liquid junction Ag/AgCl reference electrode, polyvinyl chloride (PVC) protective membrane 1007 was constructed to keep the concentration of chloride ions in the 3 M KCl inner filling solution constant. The PVC membrane solution prepared with 50 wt % PVC powder and 50 wt % 2-nitrophenyloctylether was dissolved in tetrahydrofuran (THF, Fa. Fluka) and the mixture was dropped onto a cleaned glass substrate followed by curing at room temperature (FIG. 13C). The cured membrane was transferred onto the top of the L-shaped reservoir and glued with THF. The TPP$^+$ selective membrane 1006 was prepared with a mixture of 4.4 mL of THF, 0.36 mL of dioctyl phthalate, 0.15 g of PVC and 6 mg of Na+TPB– (tetraphenylboron), and poured onto a glass substrate. The mixture was evaporated slowly at room temperature for a few hours. The membrane 1006 was carefully glued to the top of the TPP$^+$ reservoir with THF. The second PDMS layer having two openings and four access holes was placed on top of the membranes to secure the bonding of membranes between PDMS layers by pressing down the membranes (FIG. 13D). Two inner filling solutions (10 mM TPP$^+$Cl$^-$, 3 M KCl) were introduced into two L-shaped reservoirs through access holes by means of syringes and rubber tubes 1020 (FIG. 13E). Care should be taken during the introduction of the inner filling solution to avoid air bubbles, which lead to an open sensing circuit. The membranes in the two opening areas are exposed to the medium. For the sensing chamber, the third PDMS layer 1013 (4 mm thick) was bonded to the top of the second layer 1008 with a chamber volume of 85 μL (FIG. 13F). The volume of 85 μL is 2 orders of magnitude smaller than traditional experiments.

While the microfluidic sensor device has largely been described in the context of using an ion selective membrane together with an electrode, there are alternative embodiments of using other sensing modalities to analyze mitochondrial bioenergetics and more specifically measure the mitochondrial membrane potential ΔΨm of the sample. The sample may contain mitochondria present in intact cells or, alternatively, the sample may contain isolated or enriched mitochondria. For example, in one alternative, one or more fluorescent dyes are loaded with a sample into a microfluidic device having one or more chambers therein having a volume within 0 μl to about 100 μl.

Similar to TPP$^+$, many fluorescent compounds are cationic as well as lipophilic and therefore can be used to quantitatively measure the mitochondrial inner membrane potential ($\Delta_{\psi m}$). Some of the most commonly used fluorescent dyes are rhodamine 123 (Rh123), 5,5'6,6'-tetrachloro-1,1',3,3'-tetraethylbenzamidazolocarbocyanine (JC1), tetramethylrhodamine ethyl ester (TMRE), tetramethylrhodamine methyl ester (TMRM), DiOC6 and DASPMI. These dyes can diffuse across the cell membrane easily and distribute between cellular compartments in response to the standing electrochemical gradients. For intact cells, measurements $\Delta_{\psi m}$ with fluorescent dyes can be performed by comparing the fluorescence intensity from different compartments of the cells using a CCD camera, confocal microscope, or the like.

The working principle is that when the dyes are used at low concentration, the fluorescence signal shows a linear relationship with the dye concentration and the dye distribution between cell compartments follows a Nernstian relationship. Using fluorescent compounds for the measurements of $\Delta_{\psi m}$ in isolated mitochondria may be accomplished by measuring the wavelength shift in fluorescence. In the case of JC-1, which is a dual color dye, a standard curve between fluorescence signal and $\Delta_{\psi m}$ can be constructed by using different bath potassium ion concentrations $[K]_{out}$ in the presence of valinomycin. In this approach, the matrix potassium concentration $[K]_{in}$ is assumed to be 120 mM and $\Delta_{\psi m}$ is calculated as $\Delta_{\psi m}=-60 \log([K]_{in}/[K]_{out})$. See M. Reers, S. T. Smiley, C. Mottola-Hartshorn, A. Chen, M. Lin, L. B. Chen, "Mitochondrial membrane potential monitored by JC-1 Dye", *Methods in Enzymology*, 260, 406-417, (1995), which is incorporated by reference herein.

If TMRM, TMRE, Rh123, which are monochromic fluorescent dye, are used in isolated mitochondria, a ratiometric approach can be used to quantify $\Delta_{\psi m}$. More specifically, because these three dyes show a red shift in their excitation/emission fluorescence spectra when they are uptaken by the mitochondria, the amount of the wavelength shift can be used to determine the dye distribution across the mitochondrial membrane and therefore can be used to calculate $\Delta_{\psi m}$. See R. C. Scaduto, Jr., L. W. Grotyohahn, "Measurement of Mitochondrial Membrane Potential Using Fluorescent Rhodamine Derivatives", *Biophysical Journal*, 76, 469-477, (1999), which is incorporated by reference herein. DiOC6 and DASPMI are other dyes commonly used in flow cytometry for $\Delta_{\psi m}$ determination and may also be used.

In another alternative embodiment, at least one radioactive compound is added to the sample and the mitochondrial membrane potential ΔΨm of the sample is measured based at least in part on radioactivity measurements. A similar sized sample chamber volume is used in this alternative embodiment. The method of using radioactive compounds to determine $\Delta_{\psi m}$ generally involves evaluating the distribution of $^{86}$Rb$^+$ or [$^3$H]TPP$^+$ across the inner membrane in the presence of valinomycin. Theses cations distributes across the inner mitochondrial membrane in accordance with $\Delta_{\psi m}$, following a Nernstian relationship. A radiation counter device (e.g., scintillation counter) can be used to measure radioactivity.

In still another alternative embodiment, the mitochondrial membrane potential ΔΨm may be measured directly using capacitive sensing based on nanomaterials such as carbon nanotubes and graphene. Specifically, analogs of a silicon transistor can be built within a sample chamber using conventional metals such as gold, silver, or platinum as the source and drain while the nanomaterials serve as gate. The carbon nanotubes and graphene are thus conductors contained within the sample chamber. The sample chamber may have similar small volumes (e.g., between 0 μl to about 100 μl). The conductance of the conductors will change in the presence of individual mitochondria placed on top of the same in a microfluidic environment. This change correlates with $\Delta_{\psi m}$.

While embodiments have been shown and described, various modifications may be made without departing from the scope of the inventive concepts disclosed herein. The invention(s), therefore, should not be limited, except to the following claims, and their equivalents.

What is claimed is:

1. A microfluidic sensor device comprising:
a substrate having disposed thereon a reference electrode and a working electrode, wherein the reference electrode is disposed in a first solution holding region and wherein the working electrode is disposed in a second solution holding region separate from the first solution holding region; and
a sample chamber configured to hold a sample, the sample chamber separated from the first solution holding region by a polyvinyl chloride (PVC) protective member, the sample chamber separated from the second solution holding region by a membrane selective to tetraphenylphosphonium (TPP$^+$) ions.

2. The sensor device of claim 1 further comprising a voltage measuring device.

3. The sensor device of claim 1, wherein the first and second solution holding regions are defined in a PDMS layer disposed on the substrate.

4. The sensor device of claim 1, wherein the substrate comprises glass.

5. The sensor device of claim 1, wherein the membrane is formed by a mixture of tetrahydrofuran (THF), PVC, and Na$^+$TPB$^-$(tetraphnylboron sodium tetraphenylboron) that is allowed to evaporate over a substrate.

6. The sensor device of claim 1, further comprising a plurality of additional working electrodes.

7. A method of using the sensor device of claim 1 comprising:
filing the first solution holding region with KCl; and
filing the second solution holding region with tetraphenylphosphonium chloride (TPP$^+$Cl$^-$);
loading a sample solution containing mitochondria into the sample chamber; and
monitoring potential differences between the working electrode and the reference electrode.

8. The method of claim 1, further comprising loading the sample chamber with a known concentration of tetraphenylphosphonium and the method further comprised developing a calibration curve of tetraphenylphosphonium ion concentration.

9. The method of claim 7, determining tetraphenylphosphonium concentration of the sample solution based at least in part on the monitored potential differences between the working electrode and the reference electrode.

10. A method of making a microfluidic sensor device comprising:
patterning a working electrode and a separate reference electrode on a substrate;
applying a first layer of PDMS over the substrate so as to define respective openings over the working electrode and the reference electrode;
applying a membrane selective to tetraphenylphosphonium (TPP$^+$) ions the first layer of PDMS over the opening of the working electrode;
applying a PVC membrane to the first layer of PDMS over the opening of the reference electrode;
applying a second layer of PDMS over the first layer of PDMS so as to define respective openings over the membrane selective to tetraphenylphosphonium (TPP$^+$) ions and the PVC membrane; and
applying a third layer of PDMS over the second layer of PDMS, the third layer of PDMS having openings corresponding to the openings in the second layer of PDMS.

11. The method of claim 10, further comprising filling the region overlying the working electrode with a solution of tetraphenylphosphonium and filling the region overlying the reference electrode with a KCl solution.

12. A microfluidic sensor device comprising:
a substrate having patterned thereon at least one Ag/AgCl electrode;
an inner chamber overlying the at least one Ag/AgCl electrode;
a membrane selective to tetraphenylphosphonium (TPP$^+$) ions disposed on one side of the first chamber; and
a sensing chamber overlying the membrane.

13. The microfluidic sensor device of claim 12 further comprising a voltmeter coupled to a reference electrode configured for placement in the sensing chamber and the Ag/AgCl electrode.

14. The microfluidic sensor device of claim 12, wherein the inner chamber is defined at least in part by a first PDMS layer disposed on the substrate.

15. The microfluidic sensor device of claim 14, wherein the sensing chamber is defined at least in part by a second PDMS layer disposed on the first PDMS layer.

16. The microfluidic sensor device of claim 12, wherein the substrate comprises silicon.

17. A method of using the sensor device of claim 12 comprising:
filing the inner chamber with a solution containing tetraphenylphosphonium (TPP$^+$) ions;
loading a sample solution containing mitochondria into the sensing chamber;
placing a reference electrode in the sensing chamber; and
monitoring potential differences between the at least one Ag/AgCl electrode and the reference electrode.

18. A method of making a microfluidic sensor device comprising:
patterning a plurality of contact electrodes on a substrate at different test regions;
forming a silver/silver chloride electrode at each test region, the silver/silver chloride electrode electrically connected to at least one contact electrode;
forming a first PDMS layer comprising a plurality of microfluidic channels containing a hole therein;

applying the first PDMS layer to the substrate so that the silver/silver chloride electrodes are surrounded by the holes in the first PDMS layer;

applying membranes selective to tetraphenylphosphonium (TPP$^+$) ions to the first PDMS layer over each hole; and applying second and third PDMS layers over the first PDMS layer, wherein the second and third PDMS layers have respective holes corresponding to the locations of the holes in the first PDMS layer.

19. The method of claim 18, wherein the substrate comprises silicon.

20. The method of claim 18, wherein the substrate comprises at least six separate test regions.

21. The method of claim 18, wherein the membranes are first formed on a separate scaffold and transferred to the first PDMS layer.

22. A method for analyzing mitochondrial bioenergetics comprising:
provinding a microfluidic device having first chamber containing an electrode therein and a second chamber separated from the first chamber by an ion selective membrane;
loading the second chamber with a sample containing mitochondria;
measuring the voltage using the electrode; and determining the membrane potential based at least in part on the measured voltage.

23. The method of claim 22, wherein the second chamber contains a volume less than 100 µL.

24. The method of claim 22, wherein the sample containing mitochondria has a concentration below 1 ng µL$^{-1}$.

25. A method of for analyzing mitochondrial bioenergetics comprising:
providing a microfluidic device having at least one chamber therein with a volume between 0 µl and about 100 µl;
loading the at least one chamber with a sample containing mitochondria; and
measuring the mitochondrial membrane potential ΔΨm of the sample.

26. The method of claim 25, wherein the sample contains at least one fluorescent compound and the mitochondrial membrane potential ΔΨm of the sample is measured based at least in part on fluorescent intensity.

27. The method of claim 25, wherein the sample contains at least one fluorescent compound and the mitochondrial membrane potential ΔΨm of the sample is measured based at least in part on fluorescent shift.

28. The method of claim 25, wherein the sample contains at least one radioactive compound and the mitochondrial membrane potential ΔΨm of the sample is measured based at least in part on radioactivity measurements.

29. The method of claim 25, wherein the at least one chamber contains a conductor therein and the mitochondrial membrane potential ΔΨm of the sample is measured based at least in part on measured conductance of the conductor.

* * * * *